(12) United States Patent
Grimberg et al.

(10) Patent No.: US 9,778,245 B2
(45) Date of Patent: Oct. 3, 2017

(54) DIAGNOSTIC DEVICES AND METHODS

(71) Applicant: Case Western Reserve University, Cleveland, OH (US)

(72) Inventors: Brian T. Grimberg, Cleveland, OH (US); Robert Deissler, Cleveland, OH (US); William Condit, Cleveland, OH (US); Robert Brown, Cleveland, OH (US); Jason Jones, Cleveland, OH (US); Richard Bihary, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/425,729

(22) Filed: Feb. 6, 2017

(65) Prior Publication Data

US 2017/0146513 A1     May 25, 2017

Related U.S. Application Data

(63) Continuation of application No. 14/766,523, filed as application No. PCT/US2014/015604 on Feb. 10, 2014, now Pat. No. 9,575,052.

(60) Provisional application No. 61/762,602, filed on Feb. 8, 2013.

(51) Int. Cl.
G01N 33/48 (2006.01)
G01N 33/49 (2006.01)

(52) U.S. Cl.
CPC ............. *G01N 33/48* (2013.01); *G01N 33/49* (2013.01)

(58) Field of Classification Search
CPC ................................ G01N 33/48; G01N 33/49

USPC ........................................................... 356/39
See application file for complete search history.

(56) References Cited

U.S. PATENT DOCUMENTS

| | | | |
|---|---|---|---|
| 5,978,694 A | * 11/1999 | Rapoport | G01R 33/16 324/693 |
| 7,639,359 B2 | 12/2009 | Chung et al. | |
| 8,214,006 B2 | 7/2012 | Newman et al. | |
| 8,423,104 B2 | 4/2013 | Wiseman et al. | |

(Continued)

OTHER PUBLICATIONS

Chung et al.; Magneto-optic measurement of Brownian relaxation of magnetic nanoparticles; Journal of Magnetism and Magnetic Materials 320; 2008; pp. 91-95.

*Primary Examiner* — Roy M Punnoose
(74) *Attorney, Agent, or Firm* — Tarolli, Sundheim, Covell & Tummino LLP

(57) ABSTRACT

A diagnostic device is provided that comprises a light source for transmitting a light beam through a blood sample to a light detector, and a permanent magnet, wherein one of the permanent magnet and blood sample is automatically movable relative to the other between a "HIGH" magnetic state position and a "LOW" magnetic state position, such that a substantially high magnetic field is applied to the blood sample causing any hemozoin in the blood sample to tend toward perpendicular orientation to the substantially magnetic field and the suppression, or enhancement of light based on its polarization, and a zero-to-near-zero magnetic field is applied to the blood sample causing the randomization of any hemozoin in the blood sample and a baseline amount of light to pass through the blood sample in the "LOW" magnetic state position.

22 Claims, 14 Drawing Sheets

(56) References Cited

U.S. PATENT DOCUMENTS

| | | | |
|---|---|---|---|
| 2006/0025659 A1* | 2/2006 | Kiguchi | A61B 5/14558 600/316 |
| 2010/0149519 A1* | 6/2010 | Toofan | A61B 5/0059 356/51 |
| 2012/0326104 A1* | 12/2012 | Kwon | B82Y 20/00 252/583 |
| 2015/0125873 A1* | 5/2015 | Newman | G01N 27/745 435/7.1 |

* cited by examiner

DIAGNOSTIC DEVICES AND METHODS

RELATED APPLICATIONS

The present application is a continuation of U.S. patent application Ser. No. 14/766,523, filed Aug. 7, 2015, which is a U.S. National Stage application under 35 USC 371, claiming priority to PCT Application No. PCT/US2014/015604, filed on Feb. 10, 2014; which claims priority to U.S. Provisional Patent Application No. 61/762,602 filed Feb. 8, 2013, the entirety of all three applications are incorporated herein by reference.

GOVERNMENT FUNDING

This invention was made with government support under Grant No. 506274/52718394 awarded by the Coultier Foundation/CTSC. The United States government has certain rights to the invention.

FIELD OF THE INVENTION

The present invention relates generally to disease diagnosis of magnetically active microbes, and particularly relates to malaria diagnostic devices and methods.

BACKGROUND

More than three billion people live with the threat of malaria throughout the world, which results in a significant impact on economic global economic productivity. While significant progress against malaria has been observed in the past 5 years, strategies to quantify this progress are elusive because of the limitations of malaria diagnosis. The elimination of malaria in challenging endemic settings will require new approaches to understand the sustained transmission of *Plasmodium*. Efforts to eradicate malaria have been stymied because of an inability to screen populations efficiently and at an affordable cost in malarious regions which arguably contributes to a poorly directed parasite control effort and malaria resurgence.

Present methods for malaria diagnosis by microscopy take approximately 1 hour and are often confounded by the availability of expert rnicroscopists, low parasitemia, and mixed *Plasmodium* species infections. The low sensitivity of light microscopy has been an issue for some time. Significant levels of error have been shown in the microscopic diagnosis of malaria with false positive rates and false negatives as high as 50. Antigen-based RDTs have made significant contributions to malaria epidemiological and clinical studies. Although the tests are relatively easy to perform and can provide a diagnostic result in 15-20 minutes in the setting where blood samples are collected (rural villages and health outposts to clinical laboratories), they are quite costly. The RDTs, however, do not reliably detect parasites at low parasitemia (<200 parasitized cells/μL), they are less sensitive in detecting *P. vivax*, and their detection of *P. malariae* and *P. ovale* is uncertain. Additionally, as with conventional microscopy, the utility of RDTs would only be useful in malaria elimination efforts during pre-elimination time periods.

SUMMARY OF THE INVENTION

The present invention relates to malalia diagnostic devices and methods. In one example, a diagnostic device is provided that complises a light source for transmitting a light beam through a blood sample to a light detector, and a permanent magnet, wherein one of the permanent magnet and blood sample is automatically movable relative to the other between a "HIGH" magnetic state position and a "LOW" magnetic state position. A substantially high magnetic field is applied to the blood sample in the "HIGH" magnetic state position causing the olientation of any hemozoin in the blood sample to tend toward being generally perpendicular to the field direction, and the suppression of at least a portion of the light beam if the light polarization is predominantly collinear with the field direction, and an enhancement to at least a portion of the light beam if the polarization is perpendicular to the field direction. A zero-to-near-zero magnetic field is applied to the blood sample causing the randomization of any hemozoin in the blood sample in the "LOW" magnetic state position and a baseline amount of light to pass through the blood sample. The diagnostic device also comprises a sampling device that samples the light detector at the "HIGH" magnetic state position and the "LOW" magnetic state position to determine a difference measurement that c01 responds to an amount of parasitemia in the blood sample.

In another example, a diagnostic device is provided that comprises a light source for transmitting a light beam through a blood sample to a light detector, a first magnet and a second magnet. The first magnet is moved between a first adjacent side of the blood sample in a "HIGH" magnetic state position and away from the first adjacent side of the blood sample in a "LOW" magnetic state position. The second magnet is moved to a second adjacent side of the blood sample, opposite the first adjacent side of the blood sample, in a "HIGH" magnetic state position and away from the second adjacent side of the blood sample in a "LOW" magnetic state position. A substantially high magnetic field is applied to the blood sample in the "HIGH" magnetic state position causing the orientation of any hemozoin in the blood sample to tend toward being generally perpendicular to the field direction, and the suppression of at least a portion of the light beam if the light polarization is predominantly collinear with the field direction, and an enhancement to at least a portion of the light beam if the polarization is perpendicular to the field direction. A zero-to-near-zero magnetic field is applied to the blood sample causing the randomization of any hemozoin in the blood sample in the "LOW" magnetic state position and a baseline amount of light to pass through the blood sample. The substantial magnetic field applied to the blood sample moves from the first magnet to the second magnet to create a controlled directional magnetic field through the blood sample in the "HIGH" magnetic state position. The device also includes a controller that samples the light detector at the "HIGH" magnetic state position and the "LOW" magnetic state position to determine a difference measurement that corresponds to an amount of parasitemia in the blood sample.

In yet a further example, a pollable malaria diagnostic device is provided that comprises one or more batteries for providing power to components of the device, a blood sample holder for holding a blood sample, a light source for transmitting a light beam through a blood sample placed in the blood sample holder to a light detector, and a rotational magnet assembly. The rotational magnet assembly comprises a first rotational magnet holder having one or more permanent magnets disposed therein, a second rotational magnet holder having one or more permanent magnets disposed therein and being affixed by a shaft and spaced apart from the first rotational magnet holder, such that first rotational magnet holder is positioned adjacent a first side of the blood sample holder and the second rotational magnet holder is positioned adjacent a second side of the blood sample holder. The one or more permanent magnets of the first rotational magnet holder are aligned with and paired with the one or more permanent magnets of the second rotational magnet holder and configured to rotate and stay aligned with its pair counterpart during 360° rotations.

The rotational magnet assembly further comprises a motor coupled to the first and second rotational magnet holder assemblies by the central shaft and configured to rotate the first and second rotational magnet holder assemblies through 360° rotations between one or more "HIGH" magnetic state positions and one or more "LOW" magnetic state positions, such that a substantially high magnetic field is applied to the blood sample causing the alignment of any hemozoin in the blood sample generally perpendicular to the substantially high magnetic field and the suppression of at least a portion of the light beam if hemozoin exists in the blood sample in the "HIGH" magnetic state position, and a zero-to-near-zero magnetic field is applied to the blood sample causing the randomization of any hemozoin in the blood sample and a baseline amount of light to pass through the blood sample in the "LOW" magnetic state position. The device also includes a controller configured to control the rotations of the motor and sample the light detector at the one or more "HIGH" magnetic state positions and the one or more "LOW" magnetic state positions to determine a difference measurement that corresponds to an amount of parasitemia in the blood sample.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
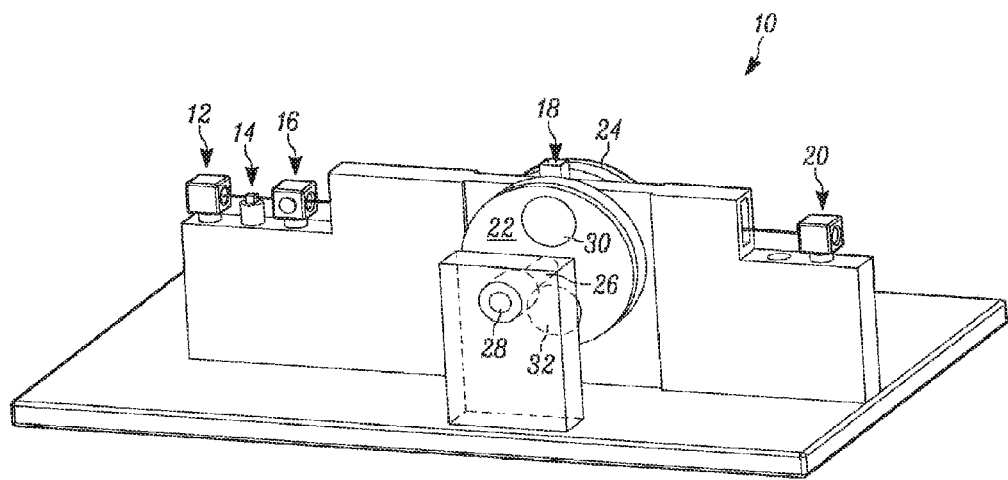
FIG. 1 illustrates a partial setup of an example of a malaria diagnostic device.

The present invention relates to devices and methods for the detection of magnetically active microbes (e.g., ~-haematin and haemozoin). One example illustrated in following paragraphs relates to malaria diagnostic devices and methods, but other similarly magnetically active microbe devices could be employed and covered by the present invention. The example devices and methods employ magneto-optical detection (MOD) of hemozoin to provide an efficient, low cost population screening tool of malaria parasite infection by exploiting the magnetic properties of hemozoin, the parasite's digestive byproduct (malaria pigment).

MOD is an improvement over other techniques through its use of magnet fields that moves between a "HIGH" magnetic state position in which substantially strong magnetic fields are applied to a blood sample that results in hemozoin moving to an aligned state that blocks (or increases the absorption) of the transmitted light in proportion to the amount of parasitemia in the blood sample, to a "LOW" magnetic state position in which a substantially zero-to-near-zero magnetic field is applied to the blood sample that results in hemozoin returning to a randomly distributed state allowing a base line amount of light to pass through the blood sample. A zero-to-near-zero magnetic field is defined as no magnetic field or some small amount of magnetic field that does not affect the randomization or alignment of the hemozoin. An amount of light passing through the blood sample is detected in both the "HIGH" and "LOW" magnetic state positions in which a difference measurement between the two can be obtained. The difference measurement can be compared to one or more thresholds or sample results of positive and/or negative samples to determine an existence and/or a progression of malaria in the blood sample, or a lack of existence of malaria in the blood sample. Additionally, multiple readings of the light detected in the "HIGH" and "LOW" magnetic state positions can be detected and normalized to provide a more accurate and sensitive readings of the presence and/or absence of malaria.

Although examples are provided with multiple pairs of permanent magnets aligned with one another during "HIGH" magnetic state positions to create a controlled directional magnetic field, a single pair of permanent magnets, or a single magnet can be employed to provide lower quality measurements and diagnosis. Furthermore, instead of rotational magnetic holders, a linear movable holder could be employed that moves along a track. Furthermore, although most illustrative examples are shown with movable magnets that provide the "HIGH" and LOW" magnetic state positions, the blood sample alone or with a portion of the MOD assembly could be moved while the magnets remain in a fixed position to provide for the "HIGH" and LOW" magnetic state positions. Additionally, a "HIGH" magnetic state position does necessarily mean that the magnet must be directly adjacent to the blood sample to work.

FIG. 1 illustrates a partial setup of an example of a malaria diagnostic device 10. The malaria diagnostic device 10 includes a laser light source 12 that provides a light beam that is polarized by a polarizer 14 and transmitted to a splitter/laser power detector 16. The polarizer 14 can be a linear polarizer. Alternatively, the polarizer 14 can be a circular polarizer. The splitter/laser power detector 16 provides a first portion of the light beam through a lysed blood sample 18 positioned in a sample location to a light photodetector 20 located on an opposite side of the blood sample 18 and aligned with the first portion of the light beam. The splitter in the splitter/laser power detector 16 provides a second portion of the light beam to a second light photodetector or power photodetector that also resides in the splitter/laser power detector 16 apparatus to measure laser power fluctuations.

A first rotational magnet holder 22 is located on a first adjacent side of the lysed blood sample 18, and a second rotational magnet holder 24 is located on a second adjacent side of the lysed blood sample 18. The first and second rotational magnet holder 22 and 24 both are illustrated as wheels but could be a variety of shapes, such as ovals, rectangular, square, triangular, irregular or some other shape that allows for movement of magnets between "HIGH" and "LOW" magnetic states. The first and second rotational magnet holders 22 and 24 are connected to one another by a central shaft 26 that has a first end connected to a DC motor (not shown) for rotating the first and second rotational magnet holders 22 and 24 concurrently and a bearing 28 that holds a second end of the shaft 26 in a fixed position but allows the magnet holders 22 and 24 to rotate about the shaft 26 360°.

Figure 3:
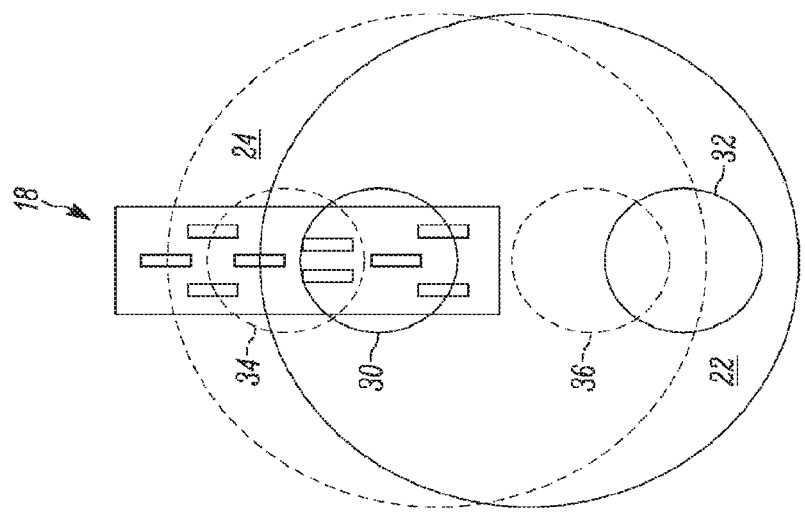
FIG. 3 illustrates first and second rotational magnet holders aligned in a "HIGH" magnetic state position.
Figure 2:
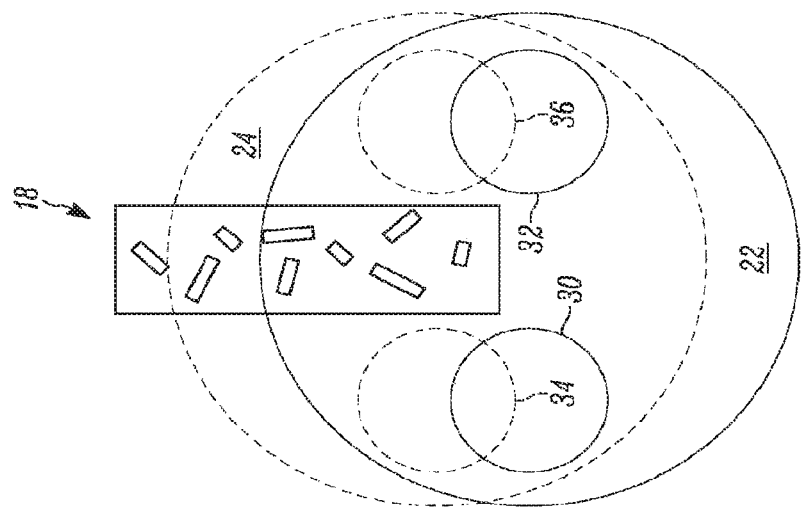
FIG. 2 illustrates first and second rotational magnet holders aligned in a "LOW" magnetic state position.

The first rotational magnet holder 22 has a first cylindrical magnet 30 positioned at a first end of the first rotational magnet holder 22, and a second cylindrical magnet 32 at a second end opposite and about 180° apart from the first end (also see FIGS. 2-3). The second rotational magnet holder 24 has a first cylindrical magnet 34 positioned at a first end of the second rotational magnet holder 24, and a second cylindrical magnet 36 at a second end opposite and about 180° apart from the first end of the second rotational magnet holder 24, such that the first magnet 30 of the first rotational magnet holder 24 is aligned with the first magnet 34 of the second rotational magnet holder 24, and the second magnet 32 of the first rotational magnet holder 22 is aligned with the second magnet 34 of the second rotational magnet holder 24.

The first magnet 30 of the first rotational magnet holder 22 has a polarity (e.g., North) that is opposite in polarity (e.g., South) of the first magnet 34 in the second rotational magnet holder 24, and the second magnet 32 of the first rotational magnet holder 24 has a polarity (e.g., South) that is opposite in polarity (e.g., North) of the second magnet 36 in the second rotational magnet holder 24. This creates a controlled directional magnetic field through the lysed blood sample 18 between the first magnet 30 of the first rotational magnet holder 22 and the first magnet 34 of the second rotational magnet holder 24 when in the 0° position, and a controlled directional magnetic field through the lysed blood sample 18 between the second magnet 32 of the first rotational magnet holder 22 and the second magnet 36 of the second rotational magnet holder 24 when in the 180° position of the 360° rotation.

Neither controlled directional field goes through the lysed blood sample 18 in the 90° and 270° position, and, therefore, the lysed blood sample 18 receives a zero-to-near-zero magnetic field in these positions. The controlled magnetic field can be increased in both control and strength by utilizing a back plate formed of a ferromagnetic material (e.g., iron, steel) behind the first and second rotational magnet holders 22 and 24 not only to provide a closed magnetic circuit but to also hold the cylindrical magnets 30, 32, 34 and 36 in their respective magnet holders.

FIG. 2 illustrates the first and second rotational magnet holders 22 and 24 aligned in a "LOW" magnetic state position (i.e., 90° or 270° position) in which a zero-to-near-zero magnetic field is applied to the lysed blood sample 18, such that the hemozoin crystals shown as block rectangles are randomly distributed in three dimensions in a cuvette when there is zero-to-near-zero magnetic field. A baseline amount of light can pass through the lysed blood sample 18 in the "LOW" magnetic state position. FIG. 3 illustrates the first and second rotational magnet holders 22 and 24 aligned in a "HIGH" magnetic state position (i.e., 0° or 180° position) in which a "HIGH" magnetic field is applied to the lysed blood sample 18, such that the hemozoin crystals shown as block rectangles tend to be oriented perpendicular to the magnetic field. This orientation reduces the transmission of light through the lysed blood sample 18, relative to the randomly distributed hemozoin crystals if the light is polarized along the field direction. It enhances the transmission of light if the light is polarized perpendicular to the field direction, relative to the randomly distributed hemozoin crystals.

The measurements or photodetector counts from the light photodetector 20 and the measurements or photodetector counts (PC2) from the laser power photodetector are sampled, for example, by a controller (e.g., microcontroller, computer). The controller utilizes the measurements from the laser power photodetector to subtract out the power fluctuations of the laser 12 from the measurements of the light photodetector 20 as needed to provide part per million sensitivity. This allows for utilization of an inexpensive light source (e.g., pen laser). The laser 12 can be a red laser that provides a wavelength between about 620 nm to about 750 nm. For example, one light source that could be employed is a 650 nm Coherent Diode Laser with a 1.5 mm spot and a linear polarizer 14 of 0.82 milliwatts yield. This type of laser has constant "average power" output through the fixed polarizer to well within 1% over many weeks, including both acceptable ambient temperature stability and intrinsic "optical mode stability" for use with a normalization-analysis, which removes these problems to a good approximation. For suppression of the light beam, the laser light is transmitted through the polarizer 14 so that the light's electric field would be collinear with the magnetic field generated by the magnets 30 and 32, or 34 and 36. For enhancement of the light beam, the light's electric field would be perpendicular to the field direction.

The controller can then determine the difference between the two measurements after the power fluctuations measured from the second photodetector 22 has been removed and compare this difference to one or more thresholds or sample results of positive and/or negative samples to determine an existence and/or a progression of malaria parasites in the blood sample, or a lack of existence of malaria parasites in the blood sample. The rotational magnet holders 22 and 24 can be repeatedly moved between the "HIGH" and "LOW" magnetic state positions to obtain a plurality of measurements for both the "HIGH" and "LOW" magnet positions. These measurements can be normalized to provide a more accurate reading of the presence and/or absence of malaria parasites.

The magnets can be permanent magnets that do not require DC power to energize and thus provides the advantage of a lower power device that can be portable. Alternatively, a single magnet can be mounted to a magnet holder that is disposed adjacent the blood sample and is rotated or moved in an out between "HIGH" and "LOW" magnetic state positions. The first and second magnet holders 22 and 24 can be made of a non-magnetic material such as aluminum, or plastic. The magnets 30, 32, 34 and 36 can be formed of any permanent ferromagnetic material, such as Neodymium iron boron. Although two magnets are shown in each magnetic holder, more or less magnets could be provided for each magnetic holder, as long as the rotation allows for zero-to-near-zero magnetic fields in the "LOW" magnetic state position.

Figure 4:
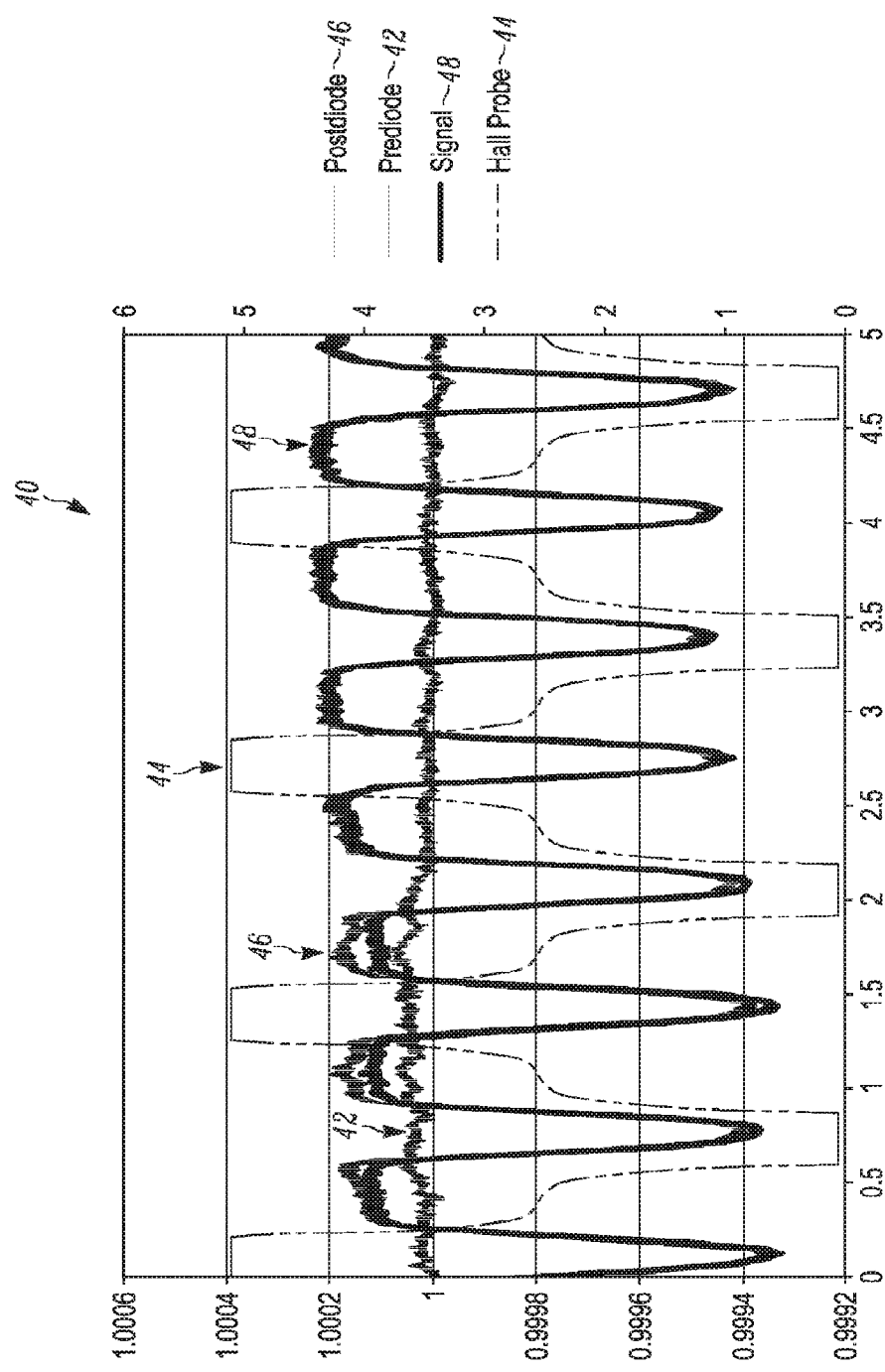
FIG. 4 illustrates a graph of amplitude versus time for a plurality of rotational magnet holder 360° measurements at about 1 to about 2 hertz between "HIGH" and "LOW" magnetic positions when malaria is present.

FIG. 4 illustrates a graph 40 of amplitude (dimensionless) versus time for a plurality of rotational magnet holder 360° measurements between "HIGH" and "LOW" magnetic positions. The Y axis is dimensionless because it has been normalized and averaged to the baseline signal so the units are (Volts/Volts). The X axis is time (seconds). The Y axis for the magnetic field is technically 1 mV/G. This is also true for FIG. 5 and FIG. 6. A first signal 42 labeled as prediode illustrates the amplitude of the laser signal at the power photodetector of the splitter/detector 16 prior to passing through the lysed blood sample 18. A second signal 44 is the magnetic field signal of the permanent magnets referred to as the hall probe. A third signal 46 is the signal out of the light photodetector 20, referred to as the post diode signal. A fourth signal 48 is the final output signal after the post diode signal is corrected by the measured power fluctuations determined by the power photodetector. As illustrated in the graph of FIG. 4, when the hall probe magnetic signal 44 is at its high and low peaks, the final output signal 48 drops a significant measurable amount illustrating the existence of hemozoin and the malaria disease. The amount that the signal drops can be measured to determine the progression of the malaria disease.

Figure 5:
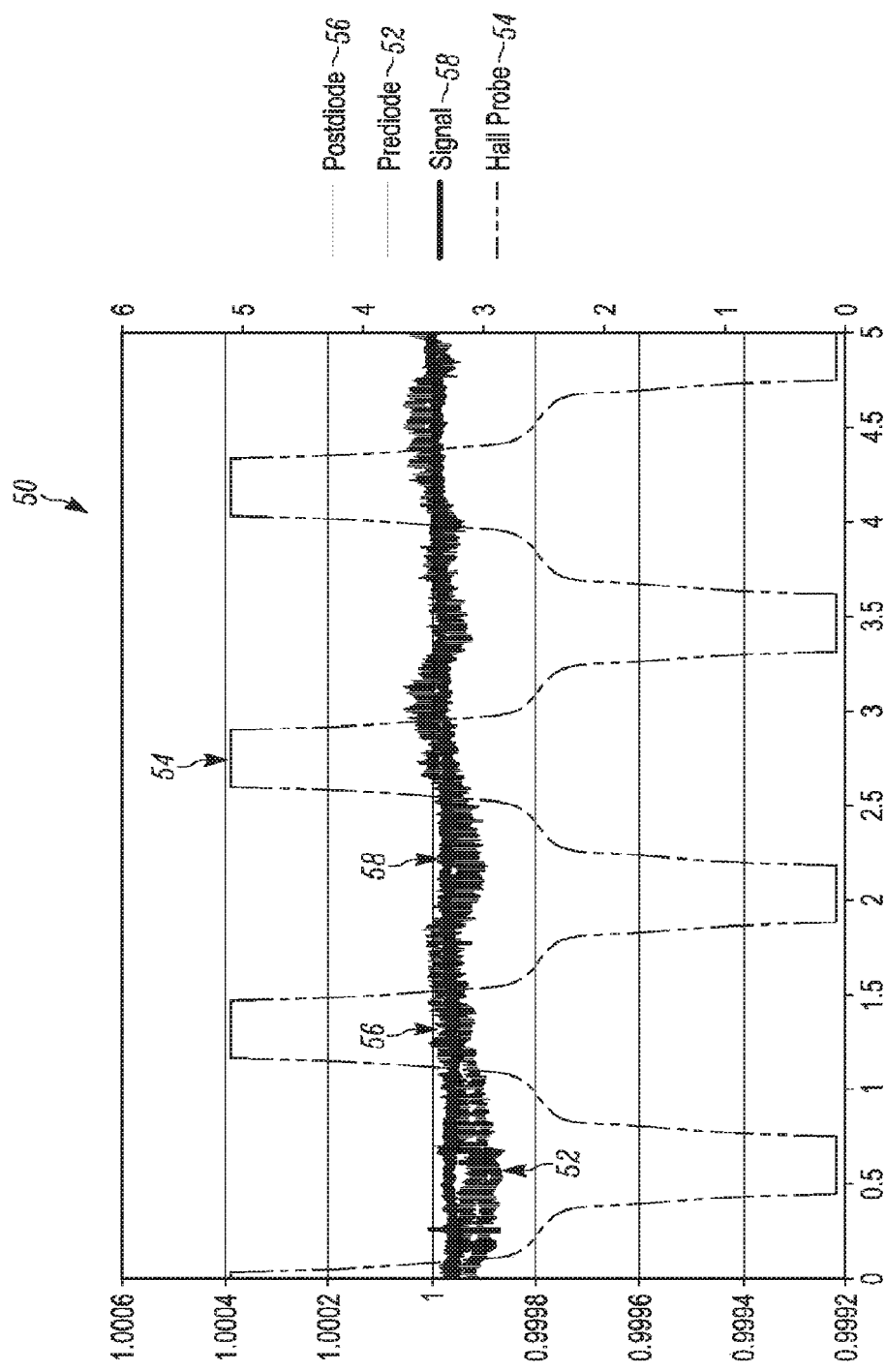
FIG. 5 illustrates a graph of amplitude versus time for a plurality of rotational magnet holder 360° measurements at about 1 to about 2 hertz between "HIGH" and "LOW" magnetic state positions when malaria is not present.

FIG. 5 illustrates a graph 50 of amplitude versus time for a plurality of rotational magnet holder 360° measurements between "HIGH" and "LOW" magnetic state positions. A first signal 52 labeled as prediode illustrates the amplitude of the laser signal at the power photodetector of the splitter/detector 16 prior to passing through the lysed blood sample 18. A second signal 54 is the magnetic field signal of the permanent magnets referred to as the hall probe. A third signal 56 is the signal out of the light photodetector 20, referred to as the post diode signal. A fourth signal 58 is the final output signal after the post diode signal is corrected by the measured power fluctuations determined by the power photodetector. As illustrated in the graph of FIG. 5, when the hall probe magnetic signal 44 is at its high and low peaks, the final output signal 48 does not change significantly from the first signal illustrating the non-existence of hemozoin and the malaria disease.

In the example of FIGS. 1-5, the hemozoin crystals are manipulated (i.e., magnetized) by pulses of magnetic flux. The pulsations are produced by placing the blood sample 18, inside a pair of rotational magnet holders 22 and 24, which moves the magnets past the blood sample. The magnetic field is produced in the gap between a pair of aligned magnets. The time interval (e.g., about 0.5 to about 1 second or about 1-2 Hertz) between the pulses is sufficiently long enough to allow the crystals to relax back into a random state. To balance the rotational magnet holders and to offer two pulsations per rotation, two magnet pairs are positioned at opposite sides of the rotational magnet holder, producing a field in the gap that is predominantly perpendicular to the plane of the magnet holder. Because the crystals tend to align generally perpendicular to the magnetic field lines, their magnetized directions are identical for both gaps of the two different pairs.

Figure 6:
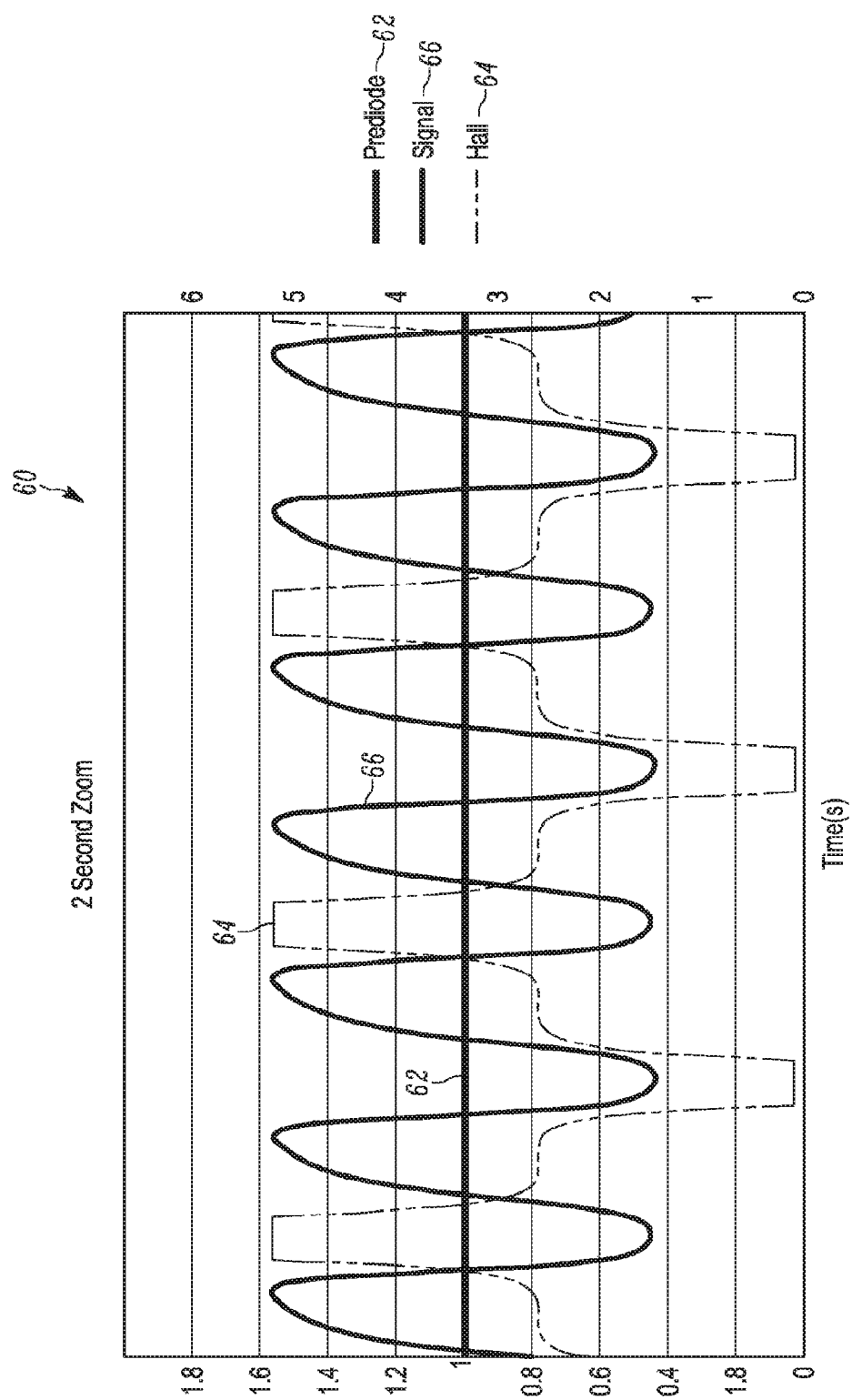
FIG. 6 illustrates a graph of amplitude versus time for a plurality of rotational magnet holder 360° measurements at about 4 to about 5 hertz between "HIGH" and "LOW" magnetic positions.

FIG. 6 illustrates a graph 60 of amplitude versus time for a plurality of rotational magnet holder 360° measurements between "HIGH" and "LOW" magnetic positions. A first signal 62 labeled as prediode illustrates the amplitude of the laser signal at the power photodetector of the splitter/detector 16 prior to passing through the lysed blood sample 18. A second signal 64 is the magnetic field signal of the permanent magnets referred to as the hall probe. A third signal 66 is the final output signal after the post diode signal is corrected by the measured power fluctuations determined by the power photodetector. The time interval (e.g., about 0.2 to about 0.25 second or about 4-5 Hertz) between the magnetic pulses is increased relative to the magnetic pulses shown in FIGS. 4 and 5, which is not sufficiently long enough to allow the crystals to relax back into a random state. As illustrated in the graph of FIG. 6, when the hall probe magnetic signal 64 is at its high and low peaks, the final output signal 66 drops a significant measurable amount illustrating the existence of hemozoin and the malaria disease. However, the slope of the back portion of the final output signal 66 is much greater than the front portion of the final output signal 66. The faster the time intervals between magnetic pulses, the more error gets introduced into the final output signal 66.

As previously stated the polarity of the magnets can be selected such that the magnetic field moves from one magnet through the blood sample to an opposing magnet at the "HIGH" magnetic state positions. In one example illustrated in cross-sectional side view of FIG. 7, a magnet holder assembly 70 including a first and a second rotational magnet holder 72 and 80, respectively, are affixed to one another by a central shaft that extends through the central axis of the first and second rotational magnet holder 72 and 80. When the magnet holders are in the 0° "HIGH" magnetic state position, a first magnet 74 of the first rotational magnet holder 62 has a positive or north pole polarity that faces a blood sample 78 and a first magnet 82 of the second rotational magnet holder has a negative or south pole polarity that faces the blood sample 78, such that a controlled directional magnetic field (B+) 88 moves from left to right from the first magnet 74 of the first magnet holder 72 to the first magnet 82 of the second magnet holder 80. Furthermore, when the magnet holders 72 and 82 ai•e in the 180° "HIGH" magnetic state position, a second magnet 84 of the second magnet holder 80 has a positive or north pole polarity that faces the blood sample 78 and a second magnet 76 of the first magnet holder 72 has a negative or south pole polarity that faces the blood sample 78, such that a controlled directional magnetic field (B−) moves from right to left from the second magnet 84 of the second magnet holder 80 to the second magnet 76 of the first magnet holder 72. In the 90° and 270° positions, a zero-to-near-zero magnetic field is applied to the blood sample allowing any hemozoin to randomize.

Figure 7:
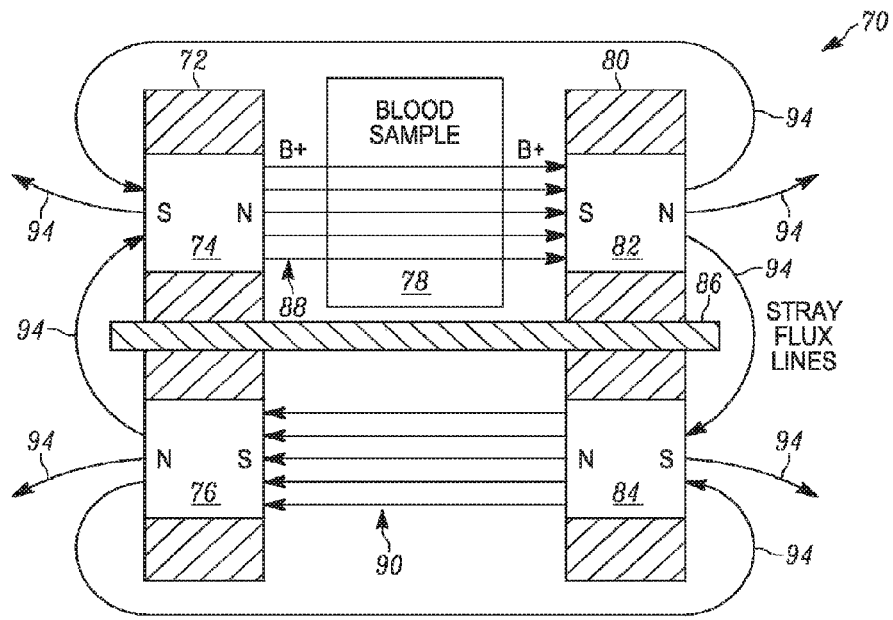
FIG. 7 illustrates an example of a cross-sectional side view of magnet holder assembly without backing plates.
Figure 8:
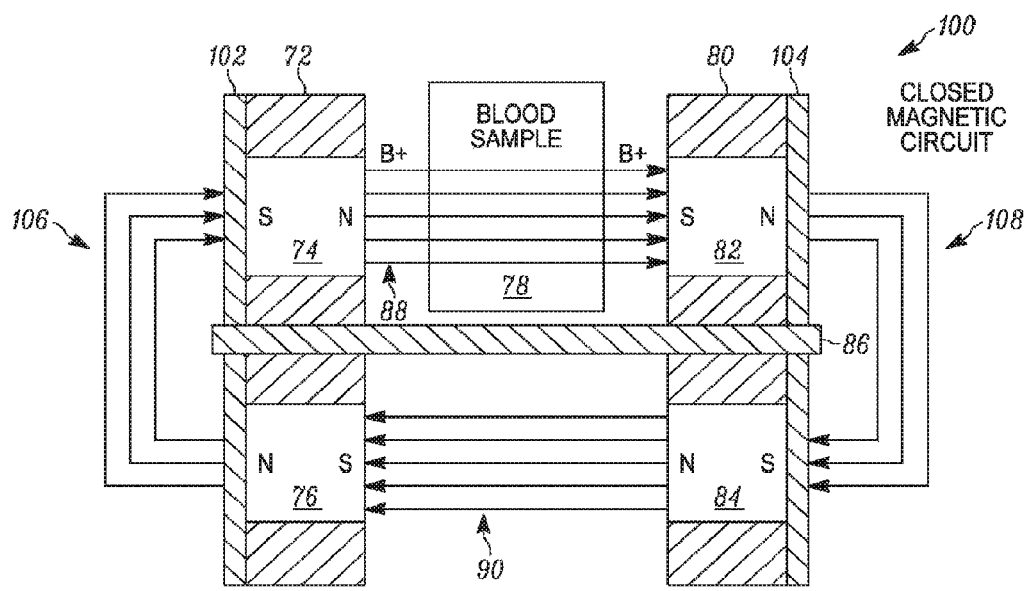
FIG. 8 illustrates an example of a cross-sectional side view of magnet holder assembly with backing plates.

As further illustrated in FIG. 7, stray flux lines escape from the poles opposite of the poles being utilized to provide the control directional magnetic field to the blood sample weakening the magnetic signal and further causing issues with other magnetically sensitive devices in the malaria detection apparatus. Therefore, the magnetic field produced in the gap of each magnet pair can be strengthened by ferromagnetic (e.g., iron, steel) backings or back plates 102 and 104 on each of the rotational magnet holders 72 and 80 of the modified rotational magnet holder assembly 100, as illustrated in FIG. 8. The ferromagnetic backings 102 and 104 hold the magnets in the rotating magnet holders, facilitates the confinement of stray flux lines, and can couple the two pairs of magnets to create a closed magnetic circuit, and shield the rest of the devices of the malaria detection apparatus from the magnetic flux. It has been found by measurement that the ferromagnetic backings increases the gap field by 25%, and the gap field is increased by another 10% if the two pairs of magnets produce fields that are anti-parallel to each other.

Figure 9:
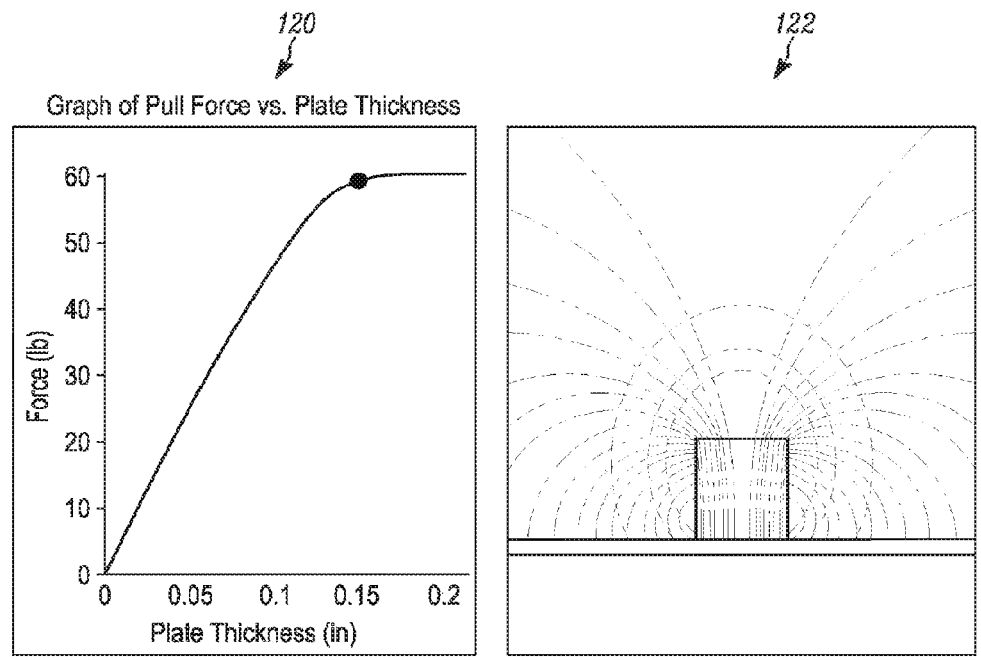
FIG. 9 illustrates a graph of plate thickness versus force of a ferromagnetic back plate with adequate thickness, while a second graph illustrates the magnetic flux lines generated and attracted to the ferromagnetic back plate and the blocking of flux lines beyond the ferromagnetic back plate due to the adequate thickness of the plate.
Figure 10:
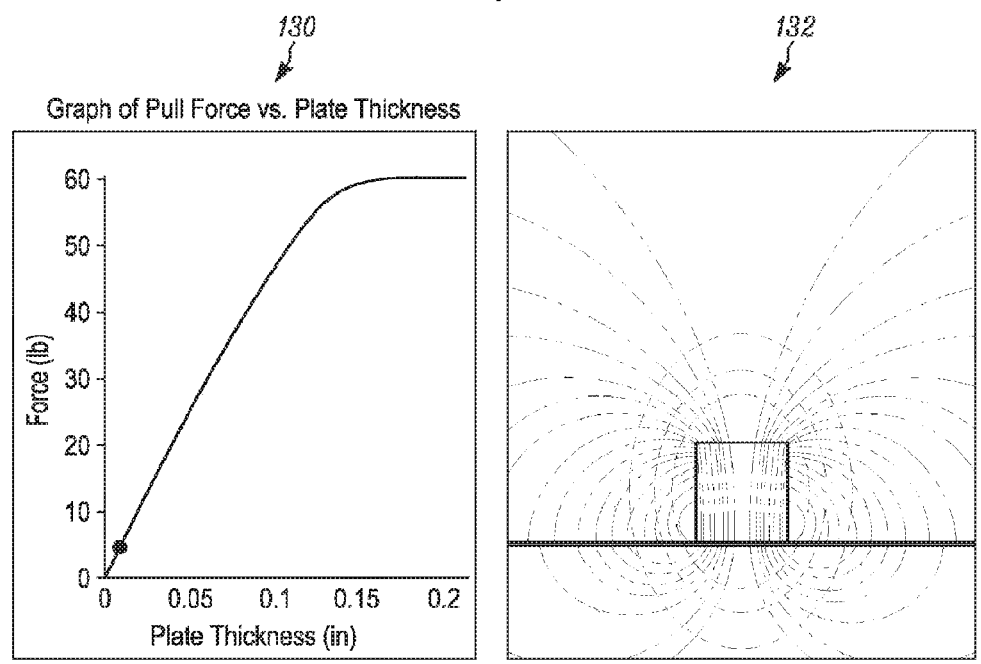
FIG. 10 illustrates a graph of plate thickness versus force of a plate with inadequate thickness, while a second graph illustrates the magnetic flux lines generated and attracted to the ferromagnetic back plate and passing flux lines beyond the ferromagnetic back plate due to the inadequate thickness of the plate.

FIG. 9 illustrates a graph 120 of plate thickness versus force of a ferromagnetic back plate with adequate thickness, while a second graph 122 illustrates the magnetic flux lines generated and attracted to the ferromagnetic back plate and the blocking of flux lines beyond the ferromagnetic back plate due to the adequate thickness of the plate. It is to be appreciated that the ferromagnetic (e.g., iron, steel) back plates should be made at a thickness so that it does not create diminishing returns for the device in terms of weight and cost. Also the second graph 122 shows how those field lines are attracted into the back plate. This ferromagnetic plate allows for a device that does not require glue or is hazardous. FIG. 10 illustrates a graph 130 of plate thickness versus force of a plate with inadequate thickness, while a second graph 132 illustrates the magnetic flux lines generated and attracted to the ferromagnetic back plate and passing flux lines beyond the ferromagnetic back plate due to the inadequate thickness of the plate. If there were electronics or detectors in the space behind the magnet, they would be susceptible to the magnetic noise caused by the passing flux lines.

Figure 11:
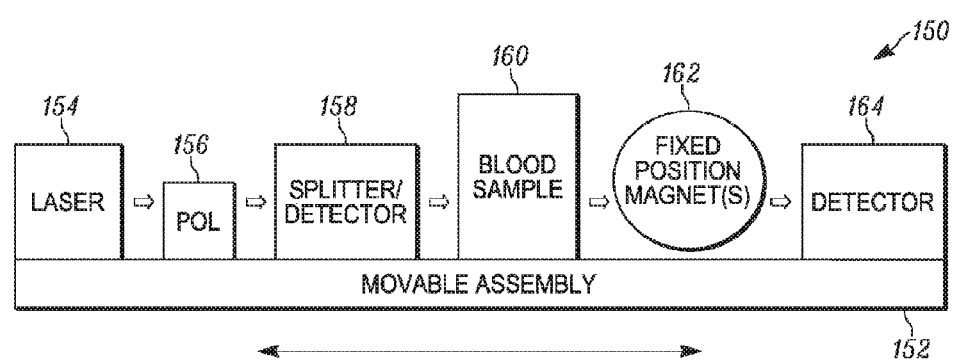
FIG. 11 illustrates a block diagram of another example malaria diagnostic device.

As previously stated, although the previous examples are illustrated with movable magnets, the magnets can be fixed in a permanent position while the blood sample and a remaining portion of one or of the MOD devices is provided as movable or a movable assembly. In this manner, the blood sample is moved back and forth between the "HIGH" and "LOW" magnetic state positions horizontally and/or vertically during sampling. FIG. 11 illustrates a block diagram of an example malaria diagnostic device 150 in which one or more magnets 162 remain in a fixed position, while the blood sample 160 or entire MOD assembly moves the blood sample between "HIGH" and "LOW" magnetic state positions. In the example of FIG. 11, a laser 154, a polarizer 156, a splitter/detector 158, a blood sample 160 and a light detector 164 reside on a movable assembly 152 and move the blood sample between the "HIGH" and "LOW" magnetic positions by moving the blood sample adjacent the one or more fixed position magnets 162 to provide a substantially strong magnetic field to the blood sample 160, and away from the one or more fixed position magnets 162 to a position that provides a zero-to-near-zero magnetic field to the blood sample 160.

Figure 12:
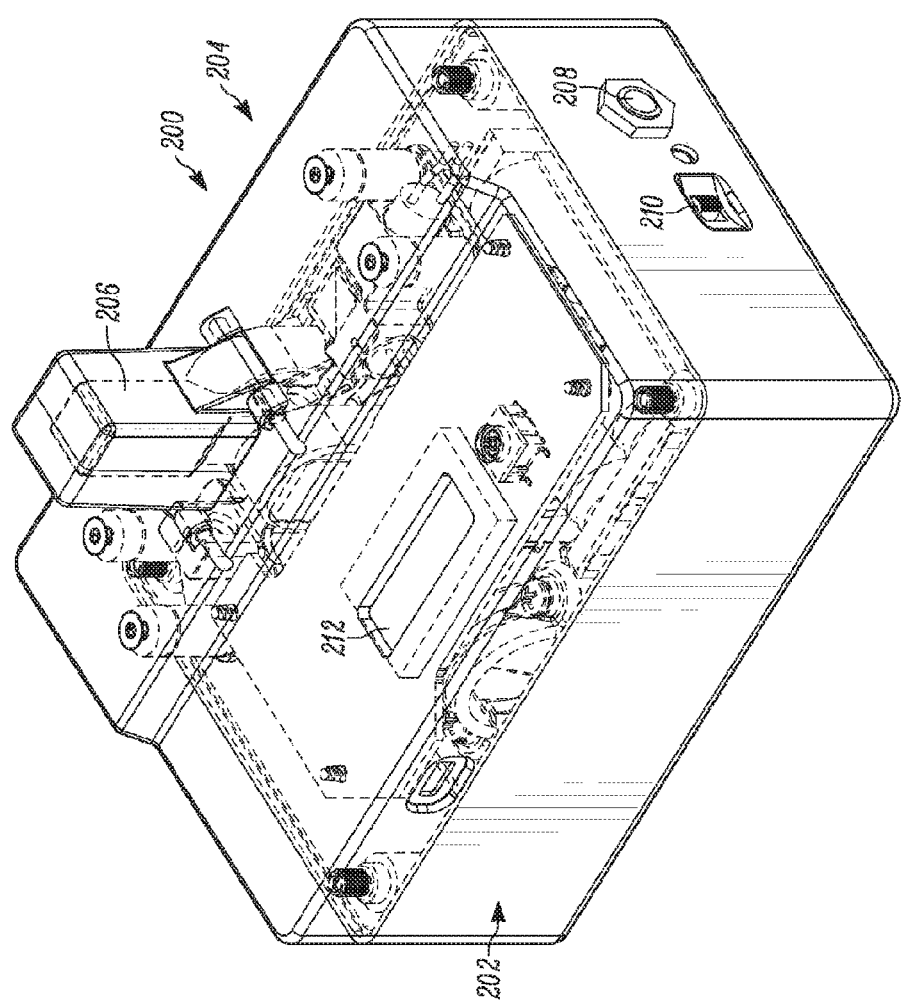
FIG. 12 illustrates a top perspective view of a portable malaria diagnostic device.
Figure 16:
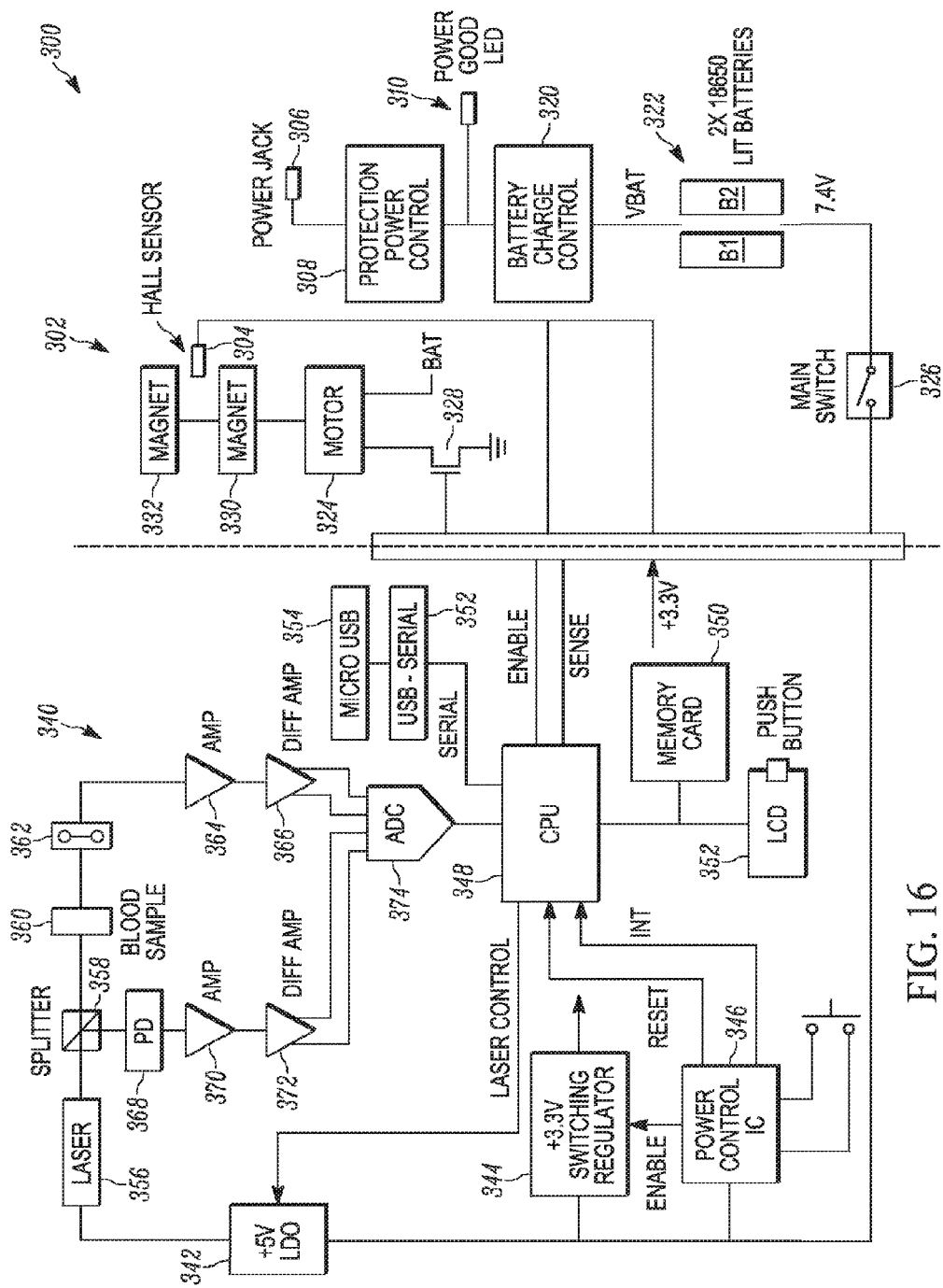
FIG. 16 illustrates an example of a schematic circuit diagram for operating the device illustrated in FIG. 12.

It is to be appreciated that the importance of a low power portable device that can be taken to rural tropical areas is realized by the present invention. FIG. 12 illustrates a top perspective view of a portable malaria diagnostic device 200. The portable malaria diagnostic device 200 includes a bottom cover 202, a top cover 204, an on/off button 210 for turning the device on and off manually, a power in jack 208 for providing power to the device and/or charging its rechargeable batteries, and a user screen 212. The user screen 212 can provide various results, instructions and/or touch screen control operator inputs based on the programming of the device. A cuvette 206 with a blood sample has been placed into a blood sample holder of the device 200. Control circuitry and power circuitry reside in the device but are not shown for simplicity sake. A schematic of one example of such circuitry is shown in FIG. 16.

Figure 13:
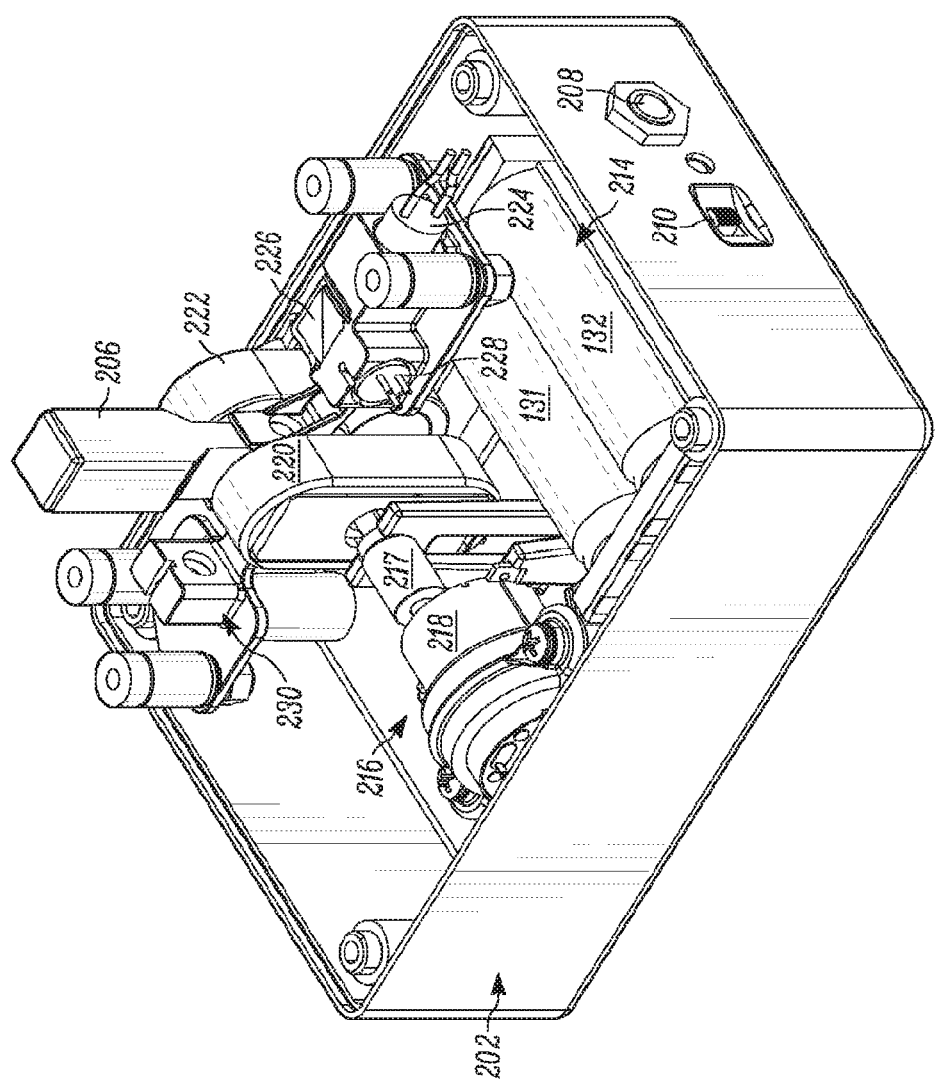
FIG. 13 illustrates a top perspective view of the portable malaria diagnostic device of FIG. 12 with the top cover removed.

FIG. 13 illustrates a top perspective view of the portable malaria diagnostic device 200 with the top cover 204 removed along with the user screen 212 and a portion of the control and power circuitry that resides beneath the user screen 212. As can be seen from the view of FIG. 13, a rechargeable battery pack 214 resides in the bottom cover 202, and includes rechargeable batteries 131 and 132 that provide power to the components of the device when an external power source is not present. A laser 224 provides light beams either continuously or pulsed during "HIGH" and "LOW" magnetic state positions through the splitter/power detector 226 and through the blood sample residing in the cuvette 206 to a light detector 230. A rotational motor driven magnet assembly 216 also resides in the bottom cover 202.

Figure 14:
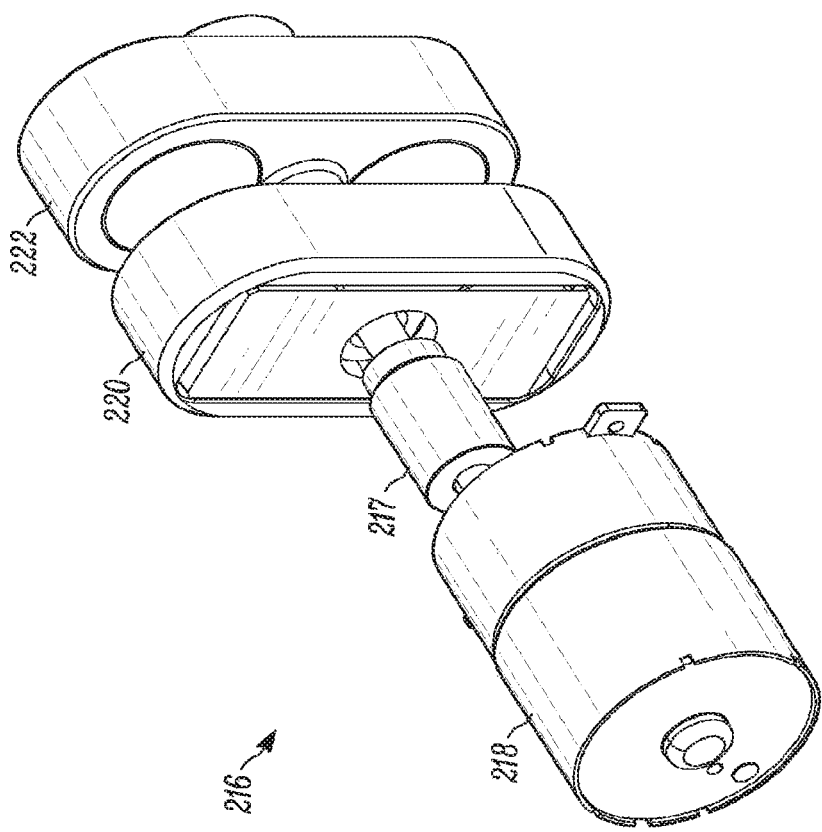
FIG. 14 illustrates a perspective view of a rotational motor driven magnet assembly.

As illustrated in both FIG. 13 and FIG. 14, the rotational motor driven magnet assembly 216 includes a DC motor 218 powered by the battery pack 214 that rotates a first and second rotational magnet holder assemblies 220 and 222 by a central axis drive shaft 217 that is held on its opposite end by a bearing. The first and second rotational magnet holder assemblies 220 and 222 are rotated by the DC motor 360° to move a first and a second pair of aligned permanent magnet pairs through "HIGH" magnetic state positions 0° and 180°, and "LOW" magnetic state positions 90° and 270° as previously discussed, while the amount of light from the laser through the lysed blood sample is continuously or periodically sampled from the light detector during the 360° rotations.

Figure 15:
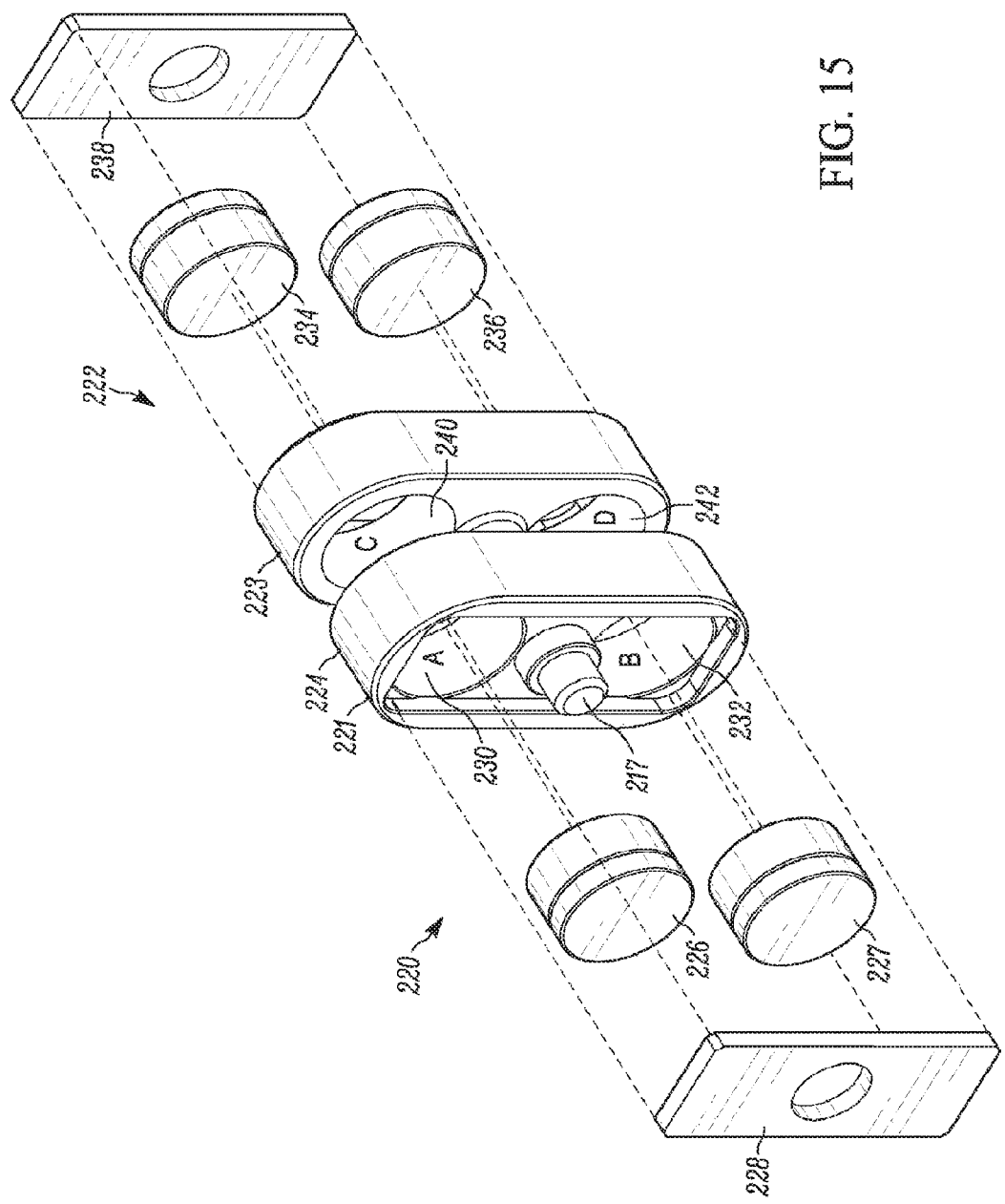
FIG. 15 illustrates an exploded view of first and second rotational magnet holder assemblies.

FIG. 15 illustrates an exploded view of the first and second rotational magnet holder assemblies 220 and 222. The first rotational magnet holder assembly 220 includes a first rotational magnet holder 221 that has a generally oval shape and includes a first recess 230 (A) for receiving a first cylindrical magnet 226 and a second recess 232 (B) for receiving a second cylindrical magnet 227. A first ferromagnetic back plate 228 holds the first cylindrical magnet 226 in the first recess 230 and the second cylindrical magnet 227 in the second recess 232, while concurrently mitigating stray flux lines caused by the cylindrical magnets 226 and 227. The second rotational magnet holder assembly 222 includes a second rotational magnet holder 223 that has a generally oval shape and includes a third recess 240 (C) for receiving a third cylindrical magnet 234 and a fourth recess 242 (D) for receiving a fourth cylindrical magnet 236. A second ferromagnetic back plate 238 holds the third cylindrical magnet 234 in the third recess 240 and the second cylindrical magnet 236 in the second recess 242, while concurrently mitigating stray flux lines caused by the cylindrical magnets 234 and 236.

The first rotational magnet holder 220 assembly and the second rotational magnet holder 222 assembly are held together by a shaft 217 that extends through the central axis of the first and second rotational magnet holders 220 and 222, such the first cylindrical magnet 226 and third cylindrical magnet always face one another, and the second cylindrical magnet 227 and fourth cylindrical magnet 236 always face one another during the 360° rotations of the first and second rotational magnet holder assemblies 220 and 222.

It is to be appreciated that mechanical features of the device have been implemented to reduce vibration and noise in the system, especially in the optical assembly. The detectors and laser have been isolated from the motor and the outside world to avoid reflections, and vibrations. This was done through low-cost shock mounts, putting the optics on the top of the device and the motor on the bottom of the device, putting vibration-proof grommets between the two, and a variety of other design methods.

It is to further be appreciated that since the hemozoin is effectively being pulsed, it is also possible to pulse the laser diode and reduce the power consumption. The laser can be pulsed at the same frequency as the magnet movement/rotation. The electronics determine when to pulse the laser by coordinating with the hall sensor and magnetic field. The data analysis can determine the signal using the same equation.

A feedback module on the laser inside the laser packager of the device 200 is provided to ensure stability in the laser and reduction in the reference diode noise. This technique can be sensitive down to the limit of shot noise in the system and laser (randomness of each individual photon entering the detector). The device 200 includes a voltage regulator and capacitors in front of the laser, detectors, and motor are provided to ensure no power fluctuations occur (power surges) that would disturb the signal. Essentially all of the key components have been isolated from the outside noise. A hall sensor switch is provided that acts as a lock-in amplifier of the signal. It relays the frequency of the magnet rotation to the data analysis program and it knows which frequency signals to amplify and which to ignore.

FIG. 16 illustrates an example of a schematic circuit diagram 300 for operating the device 200. The circuit 300 includes a power board 302 and a control board 340 coupled together through a connector or plug to isolate the more sensitive control circuitry from the power circuitry. The power board 302 includes a power jack 306 for receiving external power, when available, that goes through a protection power and control device 308 (e.g., overvoltage, undervoltage, reverse voltage protection) to a battery charge controller 320 that is utilized to recharge a rechargeable battery pack 322 comprised of battery B 1 and B2. A power good LED 310 provides an indication that proper controlled power is provided to the device 300. A main switch 326 is provided to provide power to the control board 340. A hall sensor 304 resides at a position in which the pair of magnets 330 and 332 that are not aligned with a blood sample 360 to provide feedback (SENSE) to a central processing unit (CPU) or controller 348 of the control board 340 on the location of the magnetic field during measurement operations. A motor 324 rotates the magnets 330 and 332 and is powered by the battery pack 322 and driven by a drive circuit 328 controlled by an enable line from the CPU 348.

The battery signal from the main switch 326 is provided to a power control circuit 346, a 3.3 volt switching regulator 344, and a +5 volt low dropout regulator 342 that powers a laser 356. The power control circuit 346 is employed to reset and interrupt the CPU 348, and the 3.3 volt switching regulator 344 is employed to power up circuitry requiring 3.3 volts. The CPU 348 provides outputs and can receive inputs from a user display 352 in the form of a light crystal display (LCD) and push button. Measurement results are stored to a memory card 350 by the CPU 348. The CPU 348 can also provide output results or receive commands through a USB-Serial output 352 coupled to a micro USB output 354. The laser 356 provides light signals through a splitter 358 which provides a first portion of the light through the blood sample 360 to a light detector 362, and a second portion to a power photodetector 368 for measuring power fluctuations.

The light detector 362 provides its output to an amplifier 364 for converting current to voltage then a differential amplifier 368 for generating a differential signal from the voltage signal, which is digitized by an analog-to-digital converter (ADC) 374 and provided to the CPU 348. The power detector 368 provides its output to an amplifier 370 for converting current to voltage then a differential amplifier 372 for generating a differential signal from the voltage signal, which is digitized by an analog-to-digital converter (ADC) 374 and provided to the CPU 348. The CPU 348 is programmed to perform the rotation, measurement, comparison and output operations as previously discussed.

Figure 17:
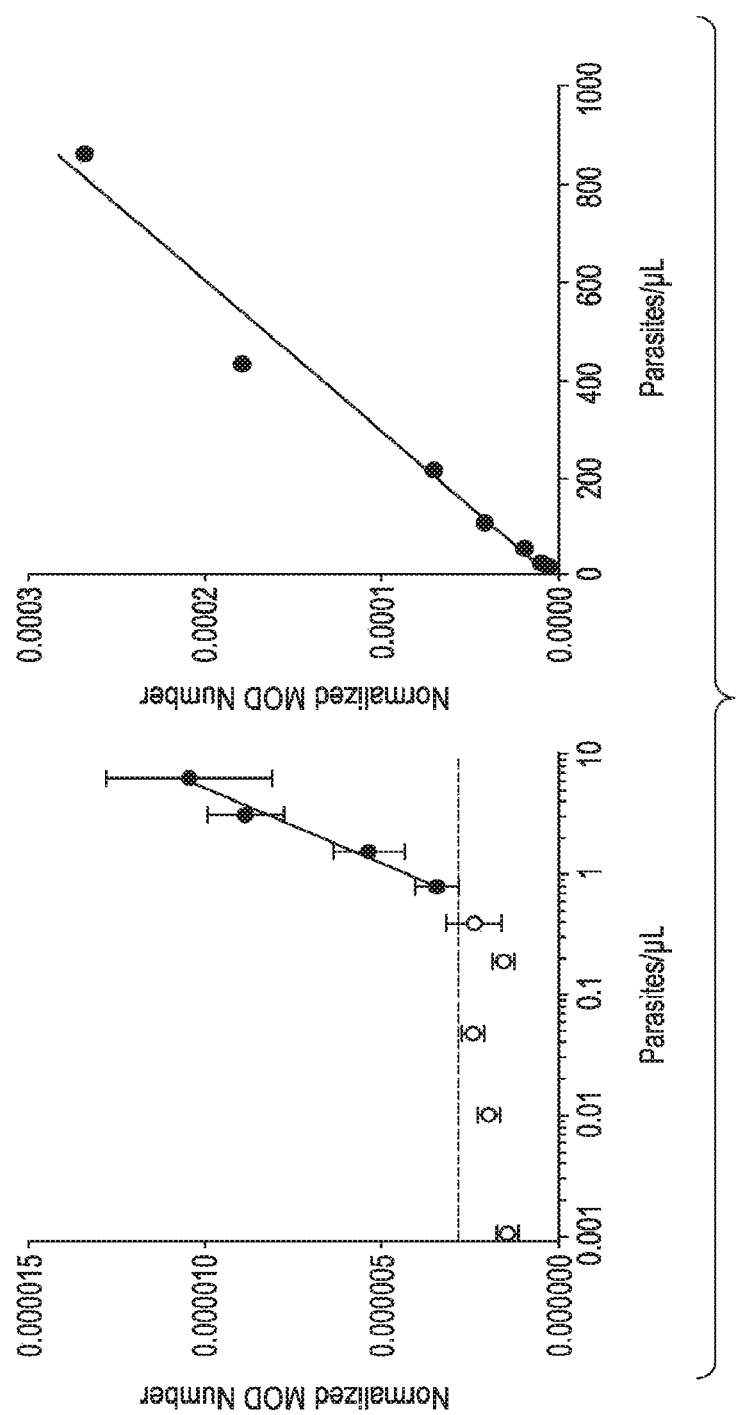
FIG. 17 shows graphs for an example of average MOD numbers from three replicate samples of cultured *P. falciparum*.

FIG. 17 shows graphs for an example of average MOD numbers from three replicate samples of cultured *P. falciparum* which were serially diluted from 800 parasites/µL down to 0.0001 parasites/µL (the entire range of dilutions is shown across BI and B2). All samples were considered to be positive (Black circles) or negative (white circles) for malaria when compared to the average MOD Number negative samples (cut off shown as dashed line in BI). The resulting Normalized MOD Numbers (which is dependent upon the amount of transmitted light) which were considered to be positive (black circles) were highly correlated to hemozoin concentration ($R2=0.9906$, $Y=8.282e{-}008*X{-}2.429e{-}006$) in panel BI and continued onto panel B2 at higher parasite levels. The lowest positive sample shown had 0.78 parasites/µL. Although there are actually error bars on the graph of FIG. 17, they are small and cannot be seen.

Figure 18:
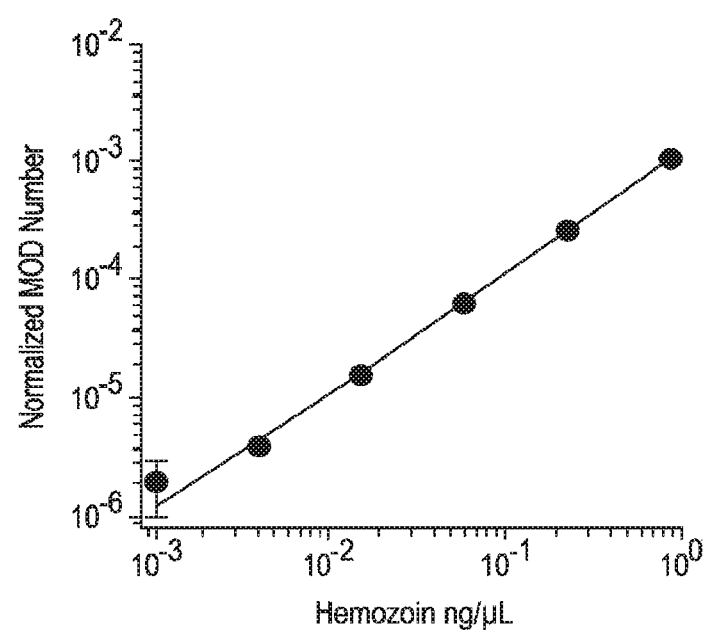
FIG. 18 illustrates a graph of hemozoin versus normalized MOD numbers for a sample of synthetic hemozoin.

Only for polarization that is collinear with the magnetic field direction will the amount of transmitted light be suppressed. For polarization perpendicular to the magnetic field, the amount of transmitted light will be enhanced. When a magnetic field is applied, the crystals tend to orient generally perpendicular to the applied field (average angle of 87.3 o±19.2 o) BI. This result is because of the anisotropic paramagnetic properties of the hemozoin crystals B2. The effect of the influence of the magnetic field is demonstrated using synthetic hemozoin shown in FIG. 18. In FIG. 18, which is a graph of hemozoin versus normalized MOD numbers, the sample of synthetic hemozoin (1 mg) was serially diluted and analyzed in triplicate on the MOD. The resulting Normalized MOD Number (which is dependent upon the amount of transmitted light) were highly correlated to hemozoin concentration ($R2=1.0$, $Y=0.001049X+2.123e{-}007$). This demonstrates that dilution of synthetic hemozoin in a sample is linear and effectively detected down to 1 pg/µL after which the samples are indistinguishable from samples containing no hemozoin. This is approximately equivalent to the amount of hemozoin that could be present in 0.33 mature parasites/µL. Although there are actually error bars on the graph on FIG. 18, they are small and cannot be seen.

References to "one embodiment", "an embodiment", "some embodiments", "one example", "an example", "some examples" and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Where the disclosure or claims recite "a," "an," "a first," or "another" element, or the equivalent thereof, it should be interpreted to include one or more than one such element, neither requiring nor excluding two or more such elements. Furthermore, what have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims.

We claim:

1. A diagnostic device comprising:
   a light source for transmitting a light beam through a sample to a light detector;
   a first permanent magnet;
   a second permanent magnet, wherein the sample and at least one of the first and second permanent magnets are movable relative to one another between a first magnetic state position and a second magnetic state position, such that a first magnetic field is directed between the first and second permanent magnets and through the sample in the first magnetic state position, and a second smaller magnetic field or a zero-to-near zero magnetic field is directed through the sample in the second magnetic state position; and
   a sampling device that samples the light detector at the first magnetic state position and the second magnetic state position to determine whether a difference measurement in received light is detected that corresponds to an amount of change in response in the sample at the first magnetic state position and the second magnetic state position.

2. The device of claim 1, wherein the sampling device takes multiple samples at the first magnetic state position and multiple samples at the second magnetic state position to determine the existence or lack of existence of disease.

3. The device of claim 1, wherein the first and second permanent magnets are moved to opposing adjacent positions to the sample in the first magnetic state position and at least one of the first and second permanent magnets are moved away from its adjacent position to the sample in the second magnetic state position by one of a linear movement and a rotational movement.

4. The device of claim 1, wherein the first permanent magnet is moved to a first side of the sample and the second permanent magnet is moved to a second side of the sample, opposite the first side, in the first magnetic state position, such that the magnetic field applied to the sample moves from the first permanent magnet to the second permanent magnet to create a substantially high controlled directional magnetic field through the sample.

5. The device of claim 1, wherein the first permanent magnet is disposed near an outside perimeter of a first rotational magnet holder, and further comprising a third permanent magnet that is disposed near an outside perimeter of the first rotational magnet holder, wherein the first permanent magnet and the third permanent magnet are spaced apart 180°, wherein the first rotational magnet holder rotates through 360° rotations and the first permanent magnet applies a magnetic field to the sample at a 0° first magnetic state position and the third permanent magnet applies a magnetic field to the sample at a 180° first magnetic state position, while the second smaller magnet field or a zero-to-near-zero magnetic field is applied to the sample at 90° and 270° second magnetic state positions.

6. The device of claim 5, wherein the first rotational magnet holder is disposed at the first side of the sample, and further comprising a second rotational magnet holder disposed at a second side of the sample opposite the first side, the second magnet holder having the second permanent magnet and a fourth permanent magnet both disposed near an outside perimeter of the second rotational magnet holder and spaced apart 180°, the second permanent magnet maintaining alignment with the first permanent magnet and the fourth permanent magnet maintaining alignment with the third permanent magnet during 360° rotations, such that a substantially high, controlled directional magnetic field passes between the first permanent magnet and the second permanent magnet at 0° first magnetic state position and a substantially high, controlled directional magnetic field passes between the third permanent magnet and the fourth permanent magnet in the 180° first magnetic state position.

7. The device of claim 6, further comprising a first ferromagnetic backing disposed on a side of the first rotational magnet holder that faces away from the sample, and a second ferromagnetic backing disposed on a side of the second rotational magnet holder that faces away from the sample, the first ferromagnetic backing holding the first and third permanent magnets in the first rotational magnet holder and also mitigating stray flux lines caused by the first and third permanent magnets, and the second ferromagnetic backing holding the second and fourth permanent magnets in the second rotational magnet holder and also mitigating stray flux lines caused by the second and fourth permanent magnets.

8. The device of claim 1, further comprising a splitter that splits the light between a first portion of the light beam being transmitted to the sample and a second portion of the light beam being transmitted to a second light detector that measures laser power fluctuations that are utilized to remove the measured power fluctuations from the measurements of the light detector by the sampling device.

9. The device of claim 1, further comprising at least one a ferromagnetic backing on an end of at least one of the first and second permanent magnets to mitigate stray flux lines.

10. The device of claim 1, wherein the first and second permanent magnets are set in a fixed position and at least one of the sample, the light source and the light detector is movable relative to the first and second permanent magnets between the first magnetic state position and the second magnetic state position.

11. A diagnostic device comprising:
    a light source for transmitting a light beam through a sample to a light detector;
    a first permanent magnet that is moved between a first adjacent side of the sample in a first magnetic state position and away from the first adjacent side of the sample in a second magnetic state position;
    a second permanent magnet that is moved to a second adjacent side, opposite the first adjacent side of the sample, in the first magnetic state position and away from the second adjacent side of the sample in the second magnetic state position, such that a controlled directional first magnetic field is applied to the sample in the first magnetic state position and a smaller or zero-to-near-zero magnetic field is applied to the sample in the second magnetic state position; and
    a controller that samples the light detector at the first magnetic state position and the second magnetic state position to determine whether a difference measurement in received light is detected that corresponds to an amount of change in response in the sample at the first magnetic state position and the second magnetic state position.

12. The device of claim 11, wherein the first and second permanent magnets are moved between the first magnetic state position and the second magnetic state position multiple times, and the controller takes multiple samples at both the first magnetic state position and the second magnetic state position to determine the existence or lack of existence of disease.

13. The device of claim 11, wherein the first permanent magnet is disposed on a first magnet holder that moves the first permanent magnet between the first and second magnetic state positions, and the second permanent magnet is disposed on a second magnet holder that moves the second permanent magnet between the first and second magnetic state positions.

14. The device of claim 13, wherein the first magnet holder is a rotational magnet holder and is disposed at a first adjacent side of the sample, and the second magnet holder is a rotational magnet holder disposed at a second adjacent side of the sample opposite the first adjacent side, the first magnet holder also having a third permanent magnet with the first and third permanent magnets both disposed near an outside perimeter of the first magnet holder and spaced apart about 180°, the second magnet holder also having a fourth permanent magnet with the second and fourth permanent magnets both disposed near an outside perimeter of the second magnet holder and spaced apart about 180°, the first permanent magnet maintaining alignment with the second permanent magnet and the third permanent magnet maintaining alignment with the fourth permanent magnet during 360° rotations, such that a controlled directional magnetic field passes between the first permanent magnet and the third permanent magnet and a controlled directional magnetic field passes between the second permanent magnet and the fourth permanent magnet.

15. The device of claim 14, further comprising a first ferromagnetic backing disposed on a side of the first magnet holder that faces away from the sample, and a second ferromagnetic backing disposed on a side of the second magnet holder that faces away from the sample, the first ferromagnetic backing holding at least one of the first and third permanent magnets in the first magnet holder and mitigating stray flux lines caused by the at least one of the first and third permanent magnets, and the second ferromagnetic backing holding at least one of the second and fourth permanent magnets in the second rotational magnet holder and also mitigating stray flux lines caused by the at least one of the second and fourth permanent magnets.

16. The device of claim 11, further comprising a splitter that splits the light between a first portion of the light beam being transmitted to the sample and a second portion of the light beam being transmitted to a second light detector that measures laser power fluctuations that are utilized to remove the measured power fluctuations from the measurements of the light detector by the sampling device.

17. The device of claim 11, wherein the device is a portable battery powered device.

18. A portable malaria diagnostic device comprising:
one or more batteries for providing power to components of the device;
a sample holder;
a light source for transmitting a light beam through a sample placed in the sample holder to a light detector;
a rotational magnet assembly comprising:
a first rotational magnet holder having one or more permanent magnets disposed therein;
a second rotational magnet holder having one or more permanent magnets disposed therein and being affixed by a shaft and spaced apart from the first rotational magnet holder, such that first rotational magnet holder is positioned adjacent a first side of the sample holder and the second rotational magnet holder is positioned adjacent a second side of the sample holder, wherein the one or more permanent magnets of the first rotational magnet holder are aligned with and paired with the one or more permanent magnets of the second rotational magnet holder and configured to rotate and stay aligned with its paired counterpart during 360° rotations; and
a motor coupled to the first and second rotational magnet holder assemblies by the central shaft and configured to rotate the first and second rotational magnet holder assemblies through 360° rotations between one or more first magnetic state positions and one or more second magnetic state positions, such that a first magnetic field is applied to the sample in the one or more first magnetic state positions and a smaller or zero-to-near-zero magnetic field is applied to the sample in the one or more second magnetic state positions; and
a controller configured to control the rotations of the motor and sample the light detector at the one or more first magnetic state positions and the one or more second magnetic state positions to determine whether a difference measurement in received light is detected that corresponds to an amount of change in response in the sample at the one or more first magnetic state position and the one or more second magnetic state positions.

19. The device of claim 18, wherein the one or more permanent magnets of the first rotational magnet holder include a first permanent magnet and a third permanent magnet disposed near an outside perimeter of the first rotational magnet holder and spaced apart about 180°, and the one or more permanent magnets of the second rotational magnet holder include a second permanent magnet and a fourth permanent magnet disposed near an outside perimeter of the second rotational magnet holder and spaced apart about 180°, the first permanent magnet maintaining alignment with the second permanent magnet and the third permanent magnet maintaining alignment with the fourth permanent magnet during 360° rotations, such that a controlled directional magnetic field passes between the first permanent magnet and the second permanent magnet through the sample at 0° first magnetic state positions and a controlled directional magnetic field passes between the third permanent magnet and the fourth permanent magnet through the sample in the 180° first magnetic state positions.

20. The device of claim 19, further comprising a first ferromagnetic backing disposed on a side of the first rotational magnet holder that faces away from the sample, and a second ferromagnetic backing disposed on a side of the second rotational magnet holder that faces away from the sample, the first ferromagnetic backing holding the first and third permanent magnets in the first rotational magnet holder and also mitigating stray flux lines caused by the first and third permanent magnets, and the second ferromagnetic backing holding the second and fourth permanent magnets in the second rotational magnet holder and also mitigating stray flux lines caused by the second and fourth permanent magnets.

21. The device of claim 18, further comprising a splitter that splits the light between a first portion of the light beam being transmitted to the sample and a second portion of the light beam being transmitted to a second light detector that measures laser power fluctuations that are utilized to remove the measured power fluctuations from the measurements of the light detector by the controller.

22. The device of claim 18, wherein the motor is rotated at about 1 hertz to about 2 hertz during sampling.

* * * * *